United States Patent [19]

Harnden

[11] 3,931,198

[45] Jan. 6, 1976

[54] 2-AMINO-5-SPIRO SUBSTITUTED OXAZOLINE-4-ONE COMPOUNDS

[75] Inventor: Michael Raymond Harnden, Horsham, England

[73] Assignee: Abbott Laboratories, Chicago, Ill.

[22] Filed: Feb. 20, 1973

[21] Appl. No.: 333,599

Related U.S. Application Data

[60] Division of Ser. No. 170,652, Aug. 10, 1971, Pat. No. 3,720,681, which is a continuation-in-part of Ser. No. 27,120, April 9, 1970, abandoned, which is a continuation-in-part of Ser. No. 689,356, Dec. 11, 1967, abandoned.

[52] U.S. Cl. ............................................ 260/293.66
[51] Int. Cl.² ........................................ C07D 211/18
[58] Field of Search ................... 260/293.66, 307 A

[56] References Cited
OTHER PUBLICATIONS
J. Med. Chem., 12:919–922, (1969), Harnden et al.

J. Med. Chem., 13:305–308, (1970), Harnden et al.

*Primary Examiner*—Sherman D. Winters
*Attorney, Agent, or Firm*—Robert L. Niblack; Joyce R. Krei; Vincent A. Mallare

[57] ABSTRACT

A novel series of 2-amino-5-spiro substituted oxazolin-4-ones and intermediates for making said compounds. These compounds are prepared by first converting the appropriately substituted cycloketone to the corresponding cyclocyanohydrin; converting this compounds to the corresponding hydroxy acid; esterifying the hydroxy acid, and finally cyclizing the hydroester to form the 2-amino-5-spiro substituted oxazolin-4-one. These compounds exhibit central nervous system activity and are active as either stimulants or depressants, and some are useful as performance enhancers.

4 Claims, No Drawings

2-AMINO-5-SPIRO SUBSTITUTED OXAZOLINE-4-ONE COMPOUNDS

CROSS-REFERENCE TO RELATED APPLICATIONS

This is a division, of application Ser. No. 170,652 filed Aug. 10, 1971, now U.S. Pat. No. 3,720,681 which in turn is a continuation-in-part of co-pending application Ser. No. 27,120, filed Apr. 9, 1970, now abandoned, which was a continuation-in-part of application Ser. No. 689,356, filed Dec. 11, 1967, now abandoned.

DETAILED DESCRIPTION OF THE INVENTION

This invention is directed to a new series of chemical compounds consisting of 2-amino-5-spiro substituted oxazolin-4-ones. More specifically, this series of compounds includes those compounds having alicyclic spiro substituents at the 5-position of the oxazole ring as well as compounds having heterocyclic spiro substituents at the 5-position. All of the compounds of this invention exhibit central nervous system activity. Some of the compounds are CNS depressants. Others are stimulants.

The compounds of this invention are represented by structural Formula I:

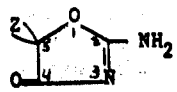

I wherein Z is a member selected from the group consisting of $C_4$ to $C_8$ cycloalkyl, lower alkyl-substituted $C_4$ to $C_8$ cycloalkyl, 4-piperidyl, lower alkyl-substituted 4-piperidyl and phenloweralkyl substituted 4-piperidyl.

The term "lower alkyl" as used herein refers to $C_1$-$C_4$ straight, branched and cycloalkyl including methyl, ethyl, n-propyl, iso-propyl, cyclopropyl, n-butyl, iso-butyl, t-butyl and cyclobutyl.

The stimulants of this invention are compounds of Formula II:

II wherein Z is 3,5-dimethylcyclohexyl, 3,3,5-trimethylcyclohexyl, or 4-(N-methylpiperidyl). The stimulants of Formula II are administered to animal in dosages of from 0.1 to 50 mg./kg. of body weight daily, preferably in divided doses.

The central nervous system depressants are represented by Formula III:

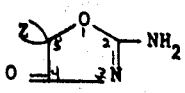

III wherein Z is $C_4$ to $C_8$ cycloalkyl, 3-methylcyclohexyl, 4-methylcyclohexyl, 3,4,5-trimethylcyclohexyl, 4-piperidyl, 1,2,6-trimethy-4-piperidyl, N-isopropyl-4-piperidyl, or N-(2-phenethyl)-4-piperidyl. The compounds are administered to animals in need of tranquilization or sedation in dosages of from 20 to 500 mg./kg. daily, preferably in divided doses.

These compounds are prepared by first reacting an appropriately substituted cycloketone with a cyanide salt of an alkali metal to form the corresponding cyclocyanohydrin. This compounds is then converted to the hydroxy acid by reaction with a strong acid, such as concentrated hydrochloric acid. The hydroxy acid derivative is then esterified by reaction with the appropriate alcohol to form an alkyl ester. This compound is then reacted with guanidine hydrochloride to form the spiro derivative.

The reactions leading to the intermediate compounds are standard reactions well known in the art, as are the intermediate compounds formed by these reactions. Thus, the cycloketones, cyclocyanohydrins, hydroxy acids and hydroxyesters are structurally familiar compounds. The 5-spiro substituted derivatives are prepared by reacting the hydroxyester derivative with guanidine in a suitable alcoholic solvent, such as methanol, ethanol, propanol and the like.

In order to better illustrate the invention disclosed herein, reference is made to the following examples which are presented to illustrate a few specific embodiments of this invention and not to limit same thereby.

EXAMPLE 1

1-Hydroxy-3,5-Dimethyl-Cyclohexane Carboxylic Acid Ethyl Ester

Part I - Cyanohydrin Derivative

A solution of 106.8 grams of sodium bisulphite in 130 ml. of water is added dropwise with stirring over 30 minutes to a stirred mixture of 100 grams of 3,5-dimethylcyclohexanone, 67.0 grams of potassium cyanide and 170 ml. of water. The reaction mixture is kept below 40° C. by means of a cold water bath. The reaction mixture is stirred for an additional 2 hours, the organic layer separated and the aqueous layer extracted with 250 ml. of ether three times. The combined organic layer and ether solutions are dried over magnesium sulfate and concentrated at reduced pressure to yield 40.3 grams of 1-hydroxy-3,5-dimethyl-cyclohexanecarbonitrile.

PART II — HYDROXY ACID

This product is then refluxed with stirring, with 300 ml. concentrated hydrochloric acid for 3 hours. The reaction mixture is concentrated at reduced pressure and the residue taken up in 250 ml. of chloroform and filtered to remove ammonium chloride. The filtrate is dried over magnesium sulfate and concentrated at reduced pressure. A syrup is obtained which upon trituration with 500 ml. of petroleum spirit and refrigeration at 50° overnight yields the crude hydroxy acid as white crystals. The crystals are filtered, dried and recrystallized from petroleum spirit to yield 9.50 grams of the pure 1-hydroxy-3,4-dimethylcyclohexane carboxylic acid.

PART III — HYDROXY ESTER

The hydroxy acid is heated under reflux with 100 ml. of ethanol and 0.05 grams of p-toluene sulphonic acid for 8 hours. The solution is concentrated at reduced pressure, the residue dissolved in 100 ml. of ether and washed with 20 ml. of 10 percent sodium carbonate and 20 ml. water. The ether solution is dried over magnesium sulfate and concentrated at reduced pressure to yield 9.43 grams of the pure 1-hydroxy-3,5-dimethylcyclohexane carboxylic acid ethyl ester.

Following the procedure of Parts I, II and III in Example 1 above, various other hydroxy acids and their corresponding alkyl esters may be prepared. Table I below lists a representative series of the hydroxy acids prepared and their accompanying physical characteristics; while Table II below lists esters prepared from the corresponding acids prepared according to the description in Part III of Example 1.

Other hydroxy acids which may be synthesized include 1-hydroxycyclopentane carboxylic acid, 1-hydroxycyclohexane carboxylic acid and 1-hydroxycycloheptane carboxylic acid, among others.

TABLE I

| Ex. | Compound | Empirical Formula | Analysis Calc. % | | Found % | | M.P. in °C | I.R. Absorption | | % yield from ketone |
|---|---|---|---|---|---|---|---|---|---|---|
| | | | C | H | C | H | | -OH cm$^{-1}$ stretch. | C=O cm$^{-1}$ stretch. | |
| 2 | (cyclobutane COOH, OH) | $C_5H_8O_3$ | 51.7 | 6.9 | 51.8 | 7.0 | 63–5 | 3500(b) | 1700 | 18.7 |
| 3 | (cycloheptane COOH, OH) | $C_9H_{16}O_3$ | 62.8 | 9.4 | 62.8 | 9.4 | 84–6 | 3530(b) | 1700 | 24.1 |
| 4 | (4-methylcyclohexane, HO, COOH) | $C_8H_{14}O_3$ | 60.8 | 8.9 | 60.8 | 8.8 | 67–86 | 3530(b) | 1700 | 34.8 |
| 5 | (3-methylcyclohexane, HO, COOH) | $C_8H_{14}O_3$ | 60.8 | 8.9 | 60.9 | 8.9 | 95–100 | 3520(b) | 1710 | 9.6 |
| 6 | (trimethylcyclohexane, HO, COOH) | $C_{10}H_{18}O_3$ | 64.5 | 9.7 | 64.7 | 9.5 | 134–6 | 3530(b) | 1700 | 33.3 |
| 7 | (tetramethylcyclohexane, HO, COOH) | $C_{11}H_{19}O_3$ | 66.0 | 10.1 | 66.2 | 10.0 | 126.9 | 3530 | 1700 | 33.1 |
| 8 | (decalin OH, COOH) | $C_{11}H_{18}O_3$ | 66.2 | 9.2 | 66.6 | 9.0 | 124–50 isomers | 3540(b) | 1700 | 23.6 |
| 9 | (norbornane OH, COOH) | $C_8H_{12}O_3$ | 61.5 | 7.8 | 61.7 | 7.7 | 123–6 isomers | 3530(b) | 1700 | 27.5 |
| 10 | (trimethylcyclohexane OH, COOH) | $C_{10}H_{18}O_3$ | 64.5 | 9.7 | 64.4 | 9.7 | 131–3 | 3520(b) | 1695 | 10.5 |

TABLE II

| HYDROXY ESTERS | |
|---|---|
| Compound | % yield from acid |
| 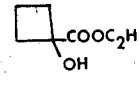 cyclobutane-COOC₂H₅, OH | 71.9 |
|  cyclopentane HO, COOC₂H₅ | 76.3 |
| 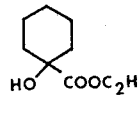 cyclohexane HO, COOC₂H₅ | 58.4 |
| 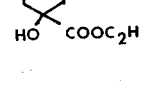 cycloheptane HO, COOC₂H₅ | 24.5 |
| 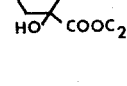 cyclooctane HO, COOC₂H₅ | 54.9 |
| 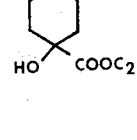 4-methyl-cyclohexane HO, COOC₂H₅ | 49.3 |
| 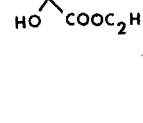 3-methyl-cyclohexane HO, COOC₂H₅ | 57.4 |
| 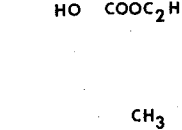 3,5-dimethyl-cyclohexane HO, COOC₂H₅ | 85.4 |
| 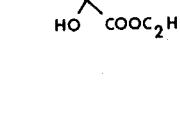 3,3,5-trimethyl-cyclohexane HO, COOC₂H₅ | 68.5 |
| 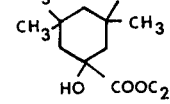 3,3,5,5-tetramethyl-cyclohexane HO, COOC₂H₅ | 58.4 |

TABLE II-continued

| Ex. | HYDROXY ESTERS Compound | % yield from acid |
|---|---|---|
| 21 | decalin with OH, COOC₂H₅ | 63.5 |
| 22 | norbornane with OH, COOC₂H₅ | 69.1 |
| 23 | 3,5,?-trimethyl-cyclohexane CH₃, CH₃, CH₃ with OH, COOC₂H₅ | 89.4 |

The spiro compounds are prepared from the corresponding hydroxyesters prepared according to Example 1. Example 24 below describes the conversion of 1-hydroxy-3,5-dimethyl cyclohexane carboxylic acid ethyl ester of Example 1 to the spiro derivative.

EXAMPLE 24

2-Amino-7,9-Dimethyl-1-Oxa-3-Aza-Spiro[4,5]Dec-2-En-4-One

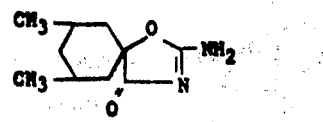

A mixture of 9.43 grams of 1-hydroxy-3,5-dimethyl-cyclohexane carboxylic acid ethyl ester with 4.38 grams of guanidine hydrochloride and 2.59 grams of potassium hydroxide pellets in 52 ml of ethanol is refluxed for 1 hour. The solution is cooled, diluted with 172 ml of water and brought to pH 7 with glacial acetic acid resulting in a white precipitate being formed. After refrigeration at 5° C for 3 hours, the crystals are filtered, washed with water and ether, and dried yielding 3.20 grams of 2-amino-7,9-dimethyl-1-oxa-3-aza-spiro[4,5]dec-2-en-4-one, having a melting point of 276°–81° C.

Elemental analysis calculated for $C_{10}H_{16}N_2O_2$: C=61.2; H=8.2; N=14.3  Found: C=61.2; H=8.3; N=14.3

Following the procedure of Example 24, other hydroxy esters, such as those described in Table II, may similarly be converted to the corresponding spiro derivatives. Table III below lists a representative series of such spiro derivatives prepared from the hydroxy esters listed in Table II and their accompanying physical characteristics.

TABLE III

| Ex. | Compound | Empirical Formula | Calc. % C | Calc. % H | Calc. % N | Found % C | Found % H | Found % N | MP in °C | I.R.Absorption Bands in 1600–1800 cm⁻¹ region | % yield from hydroxy ester |
|---|---|---|---|---|---|---|---|---|---|---|---|
| 25 | (spiro cyclobutane oxazolone NH₂) | C₆H₈N₂O₂ | 51.4 | 5.8 | 20.0 | 51.5 | 5.8 | 20.0 | 188–93 | 1660, 1740 | 15.0 |
| 26 | (spiro cyclopentane oxazolone NH₂) | C₇H₁₀N₂O₂ | 54.5 | 6.5 | 18.2 | 54.3 | 6.5 | 18.2 | 215–20 | 1660, 1720 | 16.2 |
| 27 | (spiro cyclohexane oxazolone NH₂) | C₈H₁₂N₂O₂ | 57.1 | 7.2 | 16.7 | 56.9 | 7.2 | 16.9 | 220–5 | 1660, 1720 | 16.0 |
| 28 | (spiro cycloheptane oxazolone NH₂) | C₉H₁₄N₂O₂ | 59.3 | 7.7 | 15.4 | 59.1 | 7.8 | 15.4 | 248–53 | 1660, 1720 | 21.3 |
| 29 | (spiro cyclooctane oxazolone NH₂) | C₁₀H₁₆N₂O₂ | 61.2 | 8.2 | 14.3 | 61.2 | 8.2 | 14.2 | 262–6 | 1660, 1720 | 31.2 |
| 30 | (4-methylcyclohexane spiro oxazolone NH₂) | C₉H₁₄N₂O₂ | 59.3 | 7.7 | 15.4 | 59.3 | 7.6 | 15.3 | 272–7 | 1660, 1720 | 11.3 |
| 31 | (3-methylcyclohexane spiro oxazolone NH₂) | C₉H₁₄N₂O₂ | 59.3 | 7.7 | 15.4 | 59.6 | 7.6 | 15.5 | 249–52 | 1660, 1720 | 30.7 |
| 32 | (trimethylcyclohexane spiro oxazolone NH₂) | C₁₁H₁₈N₂O₂ | 62.8 | 8.6 | 13.3 | 62.7 | 8.6 | 13.5 | 273–6 | 1665, 1730 | 14.7 |
| 33 | (tetramethylcyclohexane spiro oxazolone NH₂) | C₁₂H₂₀N₂O₂ | 64.3 | 9.0 | 12.5 | 64.6 | 9.0 | 12.3 | 318–20 | 1660, 1725 | 27.8 |
| 34 | (decahydronaphthalene spiro oxazolone NH) | C₁₂H₁₈N₂O₂ | 64.8 | 8.2 | 12.6 | 65.1 | 8.2 | 12.7 | 248–68 | 1660, 1720 | 13.3 |
| 35 | (bicyclic spiro oxazolone NH₂) | C₉H₁₂N₂O₂ | 60.0 | 6.7 | 15.6 | 59.8 | 6.6 | 15.7 | 284–9 | 1665, 1725 | 31.4 |

TABLE III-continued

| Ex. | Compound | Empirical Formula | Calc. % C | H | N | Found % C | H | N | MP in °C | I.R. Absorption Bands in 1600–1800 cm⁻¹ region | % yield from hydroxy ester |
|---|---|---|---|---|---|---|---|---|---|---|---|
| 36 | 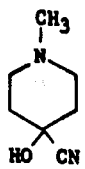 | $C_{11}H_{18}N_2O_2$ | 62.8 | 8.6 | 13.3 | 62.9 | 8.5 | 13.3 | 296–302 | 1630, 1710 | 36.4 |

The foregoing examples describe the various alicyclic spiro derivatives which form a part of this invention. The heterocyclic spiro substituents are prepared in a similar manner to that previously described herein, but for a clear understanding of this invention, the following examples are presented to further describe this novel series of compounds.

EXAMPLE 37

1-Methyl-4-Hydroxy-4-Carboethoxy Piperidine

A solution of 38.5 grams of sodium bisulphite in 100 ml of water is added dropwise over 30 minutes to a stirred mixture of 32.3 grams of 1-methyl-4-piperidone, 24.1 grams of potassium cyanide and 100 ml of water. The reaction mixture is kept below 40° C by means of a cold water bath and stirred for 2 hours during which time a white crystalline precipitate is formed. The precipitate is filtered, washed with 50 ml of water and dried in vacuo yielding 26.3 grams of 1-methyl-4-piperidone cyanohydrin.

The cyanohydrin is refluxed with stirring, with 100 ml concentrated hydrochloric acid for 3 hours. The solution is then concentrated at reduced pressure and the residue taken up in boiling alcohol, filtered hot, and the filtrate concentrated at reduced pressure to a white solid yielding 35.9 grams of 1-methyl-4-hydroxy-4-carboxy-piperidine hydrochloride.

The hydroxy acid hydrochloride is heated under reflux with 300 ml of ethanol and 0.15 grams of p-toluene sulphonic acid for 16 hours. The solution is concentrated at reduced pressure and the residue treated with 200 ml of 10 percent sodium carbonate solution, then extracted with 250 ml of chloroform three times. The chloroform solution is washed with 100 ml water, dried over magnesium sulfate and concentrated at reduced pressure. The clear liquid obtained is distilled and on cooling, solidifies to a white crystalline material yielding 16.5 grams of 1-methyl-4-hydroxy-4-carboethoxy piperidine having a boiling point of 93°–95° at 1.2 mm of pressure. Elemental analysis for $C_9H_{17}NO_3$: Calculated: C=57.7; H=9.2; N=7.5 Found: C=57.5; H=9.2; N=7.6

In Table IV below are listed a representative number of other such hydroxy acid esters prepared in accordance with the procedure of Example 37, and their characteristic physical properties.

TABLE IV

| Ex. | Compound | Empirical Formula | Calc. % C | H | N | Found % C | H | N | BP °C | IR Absorption chloroform sol. -OH stretch. | C=O stretch. | % yield from ketone |
|---|---|---|---|---|---|---|---|---|---|---|---|---|
| 38 | | $C_{16}H_{23}NO_3$ | 69.3 | 8.4 | 5.1 | 9.4 | 8.5 | 5.3 | 160–4 at 0.8 mm | 3520 | 1720 | 58.3 |
| 39 | | $C_{15}H_{21}NO_3$ | 68.4 | 8.0 | 5.3 | 8.7 | 8.1 | 5.3 | 142–8 at 0.2 mm | 3510 | 1710 | 66.4 |

TABLE IV-continued

| Ex. | Compound | Empirical Formula | Calc. % C | H | N | Found % C | H | N | BP °C | IR Absorption chloroform sol. -OH stretch. | C=O stretch. | % yield from ketone |
|---|---|---|---|---|---|---|---|---|---|---|---|---|
| 40 | [structure: N-CH3, CH3, CH3, HO, CO2C2H5 piperidine] | C₁₁H₂₁NO₃ | 61.4 | 9.8 | 6.5 | 1.4 | 0.1 | 6.6 | 111–5 at 4.0 mm | 3575 | 1720 | 62.1 |
| 41 | [structure: N-C2H5, HO, CO2C2H piperidine] | C₁₀H₁₉NO₃ | 59.7 | 9.5 | 7.0 | 9.6 | 9.5 | 6.9 | 77–80 at 0.5 mm | 3510 | 1710 | 51.7 |
| 42 | [structure: N-CH(CH3)2, HO, CO2C2H5 piperidine] | C₁₁H₂₁NO₃ | 61.4 | 9.8 | 6.5 | 1.5 | 9.8 | 6.4 | 87–103 at 1.0 mm | 3515 | 1710 | 30.2 |

The heterocyclic spiro substituents are generally prepared in the same manner as previously described for the alicyclic spiro compounds; that is, the hydroxy ester is reacted with guanidine hydrochloride in an alcoholic solvent and the product removed. Example 43 following below shows the preparation of one such heterocyclic spiro compound.

EXAMPLE 43

2-Amino-8-Methyl-3,8-Diaza-Spiro[4,5]Dec-2-En-One

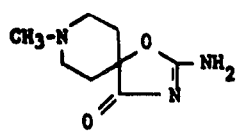

A solution consisting of 43.5 grams of sodium methoxide in 1,320 ml of ethanol is added to a solution containing 78.0 grams of guanidine hydrochloride in 330 ml of ethanol and the mixture stirred thoroughly. Sodium chloride precipitates out of solution and is removed by filtration. A solution of 150.3 grams of 1-methyl-4-hydroxy-4-carboethoxy-piperidine in 375 ml of ethanol is then added to the filtrate and the resulting solution is refluxed with stirring for 1 hour. One liter of ethanol is removed by distillation at reduced pressure and the remaining solution cooled. On cooling a crystalline precipitate forms which is filtered and dried. The filtrate is then completely evaporated at reduced pressure and the residue obtained taken up in 100 ml of fresh ethanol, cooled and additional precipitate is obtained. This procedure is repeated twice more until a total of 74.3 grams of crude product is obtained. The crude product is recrystallized from ethanol, filtered and dried, yielding 56.3 grams of 2-amino-8-methyl-3,8-diaza-spiro[4,5]dec-2-en- 4-one having a melting point of 257°–261° C. Elemental analysis for $C_8H_{13}N_3O_2$: Calculated: C=52.4; H=7.2; N=22.9 Found: C=52.2; H=7.3; N=23.0

The procedure of Example 43 may be followed to prepare other heterocyclic spiro compounds. In Table V below is listed those spiro substituents prepared from the corresponding hydroxy esters according to the procedure of Example 43 including the identifying physical characteristics of each.

TABLE V

| Ex. | Compound | Empirical Formula | Calc. % C | H | N | Found % C | H | N | MP in °C | IR Absorption bands in 1600–1800 cm⁻¹ reg. | % yield from ester |
|---|---|---|---|---|---|---|---|---|---|---|---|
| 44 | [structure: HN, O, NH2, N piperidine spiro] | C₇H₁₁N₃O₂ | 49.7 | 6.6 | 24.8 | 49.8 | 6.6 | 24.8 | 313–7 | 1625, 1710 | 32.4 |

TABLE V-continued

| Ex. | Compound | Empirical Formula | Calc. % C | Calc. % H | Calc. % N | Found % C | Found % H | Found % N | MP in °C | IR Absorption bands in 1600–1800 cm⁻¹ reg. | % yield from ester |
|---|---|---|---|---|---|---|---|---|---|---|---|
| 45 | (benzyl-piperidine spiro oxazolinone) | $C_{15}H_{19}N_3O_2$ | 65.9 | 7.0 | 15.4 | 65.6 | 7.1 | 15.6 | 253–8 | 1660, 1725 | 47.7 |
| 46 | (phenyl-CH₂-N piperidine spiro) | $C_{14}H_{17}N_3O_2$ | 64.8 | 6.6 | 16.2 | 64.7 | 6.4 | 16.0 | 225–9 | 1660, 1735 | 50.3 |
| 47 | (trimethyl substituted) | $C_{10}H_{17}N_3O_2$ | 56.8 | 8.1 | 19.9 | 57.0 | 8.3 | 19.8 | 293–8 | 1650, 1725 | 4.5 |
| 48 | (C₂H₅-N piperidine spiro) | $C_9H_{15}N_3O_2$ | 54.8 | 7.7 | 21.3 | 54.7 | 7.7 | 21.5 | 246–50 | 1680, 1730 | 37.1 |
| 49 | ((CH₃)₂CH-N piperidine spiro) | $C_{10}H_{17}N_3O_2$ | 56.8 | 8.1 | 19.9 | 56.9 | 8.2 | 20.1 | 237–44 | 1640, 1720 | 35.5 |

The foregoing 2-amino-5-substituted spiro oxazolin-4-one compounds exhibit central nervous system activity; more specifically, most of these novel compounds are central nervous system depressants. A few of the compounds disclosed herein appear to exhibit stimulant activity, rather than depressant activity.

When these compounds are administered to a group of test mice in dosages ranging up to 500 milligrams per kilogram of body weight, the mice exhibit a general decrease in activity being withdrawn and lethargic.

Table VI below details the activity of the various species of this series along with the dosages utilized expressed in mg/kg of body weight and the lethal dosage at which 50 percent of the animals expire ($LD50$) for each of the compounds. Unless otherwise indicated, the dosage and the $LD50$ were administered by intraperitoneal injection. It is to be understood, of course, that the particular route of administration is not critical to the manifestation of biological effects.

TABLE VI

| Compound | Activity | Dose in mg/kg | $LD_{50}$ in mg/kg |
|---|---|---|---|
| 6-amino-5-oxa-7-azaspiro[3,4]oct-6-en-8-one | depressant | 200 | >500 |
| 2-amino-1-oxa-3-azaspiro[4,4]non-2-en-4-one | depressant | 500 | >1000 |
| 2-amino-1-oxa-3-azaspiro[4,5]dec-2-en-4-one | depressant | 200 | >1000 |
| 2-amino-1-oxa-3-azaspiro[4,6]undec-2-en-4-one | depressant | 500 | >1000 |
| 2-amino-1-oxa-3-azaspiro[4,7]dodec-2-en-4-one | depressant | 500 | >1000 |
| 2-amino-8-methyl-1-oxa-2-azaspiro[4,5]dec-2-en-4-one | depressant | 500 | >1000 |
| 2-amino-7-methyl-1-oxa-3-azaspiro[4,5]dec-2-en-4-one | depressant | 200 | ~750 |
| 2-amino-7,9-dimethyl-1-oxa-3-azaspiro[4,5]dec-2-en-4-one | stimulant | 1 | ~300 |
| 2-amino-7,8,9-trimethyl-1-oxa-3-azaspiro[4,5]dec-2-en-4-one | depressant | 200 | >1000 |
| 2-amino-7,7,9-trimethyl-1-oxa-3-azaspiro[4,5]dec-2-en-4-one | stimulant | 0.1 | >750 |
| 2′-aminospiro[norbornane-2,5′-[2]oxazolin]-4′-one | depressant | 500 | >1000 |
| 2′-amino-octahydrospiro[naphthalene-2(1H),5′-[2] | depressant | 500 | >1000 |

TABLE VI-continued

| Compound | Activity | Dose in mg/kg | LD$_{50}$ in mg/kg |
|---|---|---|---|
| oxazolin]-4'-one | | | |
| 2-amino-1-oxa-3,8-diazaspiro[4,5]dec-2-en-4-one | depressant | 50 | >1000 |
| 2-amino-8-methyl-1-oxa-3,8-diazaspiro[4,5]dec-2-en-4-one | stimulant | 10 | >1000 |
| 2-amino-8-benzyl-1-oxa-3,8-diazaspiro[4,5]dec-2-en-4-one | depressant | 200 | >1000 |
| 2-amino-7,8,9-trimethyl-1-oxa-3,8-diazaspiro[4,5]-2-en-4-one | depressant | 20 | >500 |
| 2-amino-8-isopropyl-1-oxa-3,8-diazaspiro-[4,5]dec-2-en-4-one | depressant | 100 | 1000 |
| 2-amino-8-phenethyl-1-oxa-3,8-diazaspiro-[4,5]dec-2-en-4-one | depressant | 200 | >1000 |

In addition to the foregoing activity, the administration of some of these novel compounds to warm-blooded animals results in an increased rate of learning by the animal coupled with a prolonged period of retention of the learned behavior.

The behavioral effects resulting from the administration of these compounds to rats were evaluated on a modified Cook-Weidley apparatus (L. Cook and E. Weidley, Ann. N.Y. Acad. Sci., 66, 790, 1957). The apparatus consists of a chamber with a grid flooring and an escape platform outside the chamber. The electric shock to the grid floor was controlled by a rheostat mechanism and scrambler. Rats were divided into 2 groups for each test trial. One group was administered saline as the control and the other group the test compound about ½ hour prior to electroconvulsive shock. It is known that electroconvulsive shock induces a state of proactive amnesia or an impaired learning rate (Deutsch, J.A., 1962, Ann. Rev. Psychol., 24, 259). Then, 15 minutes after electroconvulsive shock, the rats were given 10 acquisition trials on the jump out test to measure learning rates. Each acquisition trial consisted of 15 seconds in the chamber without any stimulation followed by 10 seconds of buzzer stimulation and culminated by 5 seconds of buzzer-plus-shock stimulation. The time from entrance into the apparatus until the rat jumps out is recorded as the escape time. Retention of the learned behavioral pattern was tested by repeating the test one hour after the last acquisition trial. The test sequence for each trial was terminated upon successful completion of the task, e.g., jumping out of the chamber.

EFFECT OF 2-AMINO-8-METHYL-1-OXA-3,8-DIAZASPIRO
[4,5]DEC-2-EN-4-ONE
INTRAPERITONEAL ADMINISTRATION

| Trial | Test Cpd. — 10 mg/kg | Mean Escape Time — Sec. Control |
|---|---|---|
| 1 | 29.8 ± 0.3 | 30.0 ± 0.0 |
| 2 | 29.5 ± 0.5 | 29.3 ± 0.8 |
| 3 | 13.8 ± 1.7 | 26.0 ± 2.4 |
| 4 | 12.0 ± 2.1 | 22.0 ± 3.6 |
| 5 | 7.0 ± 1.6 | 22.3 ± 3.8 |
| 6 | 7.8 ± 1.5 | 18.5 ± 1.9 |
| 7 | 6.5 ± 1.6 | 18.0 ± 2.3 |
| 8 | 7.0 ± 2.2 | 13.0 ± 2.9 |
| 9 | 10.8 ± 3.0 | 15.6 ± 2.1 |
| 10 | 9.0 ± 1.2 | 13.9 ± 1.7 |
| Retention Trial — 1 hour after last Acquisition Trial: | | |
| | 13.8 ± 1.4 | 15.8 ± 3.3 |

EFFECT OF 2-AMINO-7,7,9-TRIMETHYL-1-OXA-3-AZASPIRO
[4,5]DEC-2-EN-4-ONE
INTRAPERITONEAL ADMINISTRATION

| Trial | Test Cpd. — 10 mg/kg | Mean Escape Time — Sec. Control |
|---|---|---|

INTRAPERITONEAL ADMINISTRATION

| Trial | Test Cpd. 20 mg/kg | Mean Escape Time — Sec. Control |
|---|---|---|
| 1 | 30.0 ± 0.0 | 30.0 ± 0.0 |
| 2 | 29.0 ± 0.4 | 29.5 ± 0.2 |
| 3 | 21.2 ± 3.0 | 19.7 ± 5.2 |
| 4 | 17.7 ± 5.4 | 20.2 ± 5.3 |
| 5 | 14.7 ± 1.8 | 18.0 ± 2.7 |
| 6 | 18.0 ± 3.9 | 18.5 ± 3.6 |
| 7 | 10.0 ± 2.1 | 20.2 ± 4.7 |
| 8 | 5.5 ± 1.8 | 16.5 ± 3.8 |
| 9 | 6.7 ± 2.5 | 18.7 ± 5.0 |
| 10 | 7.2 ± 2.8 | 13.7 ± 4.4 |
| Retention Trial — 1 hour after last Acquisition Trial: | | |
| | 8.0 ± 2.6 | 20.2 ± 3.3 |

EFFECT OF 2-AMINO-7,9-DIMETHYL-1-OXA-3-AZASPIRO
[4,5]DEC-2-EN-4-ONE
ORAL ADMINISTRATION

| Trial | Test Cpd. — 20 mg/kg | Mean Escape Time — Sec. Control |
|---|---|---|
| 1 | 30.0 ± 0.0 | 30.0 ± 0.0 |
| 2 | 29.2 ± 0.4 | 29.7 ± 0.2 |
| 3 | 20.0 ± 4.3 | 27.2 ± 1.8 |
| 4 | 7.5 ± 2.9 | 19.7 ± 2.4 |
| 5 | 4.7 ± 0.8 | 16.0 ± 3.2 |
| 6 | 7.2 ± 2.0 | 14.7 ± 3.6 |
| 7 | 8.0 ± 1.6 | 18.7 ± 4.5 |
| 8 | 10.5 ± 3.7 | 11.0 ± 2.6 |
| 9 | 7.0 ± 1.2 | 13.0 ± 3.2 |
| 10 | 7.5 ± 2.1 | 15.5 ± 4.1 |
| Retention Trial — 1 hour after last Acquisition Trial: | | |
| | 6.7 ± 1.4 | 15.7 ± 5.0 |

I claim:
1. A compound of the formula

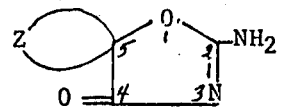

wherein Z is $C_4$ to $C_8$ cycloalkyl, 3-methylcyclohexyl, 4-methylcyclohexyl, 3,4,5-trimethylcyclohexyl, 4-piperidyl, 1,2,6-trimethyl-4-piperidyl, N-isopropyl-4-piperidyl, or N-(2-phenethyl)-4-piperidyl.

2. A compound in accordance with claim 1, said compound being 2-amino-7,8,9-trimethyl-1-oxa-3,8-diazaspiro [4.5]dec-2-en-4-one.

3. A compound in accordance with claim 1, said compound being 2-amino-1-oxa-3,8-diazaspior[4,5]-dec-2-en-4-one.

4. A compound in accordance with claim 1, said compound being 2-amino-7-methyl-1-oxa-3-azaspiro[4.5]dec-2-en-4-one.

* * * * *